United States Patent
Ji et al.

(10) Patent No.: US 11,313,790 B2
(45) Date of Patent: Apr. 26, 2022

(54) METHOD FOR DETECTING IODINE CONCENTRATION IN WATER SAMPLES

(71) Applicant: Harbin Medical University, Heilongjiang (CN)

(72) Inventors: Xiaohong Ji, Heilongjiang (CN); Yanhui Gao, Heilongjiang (CN); Yanmei Yang, Heilongjiang (CN); Dianjun Sun, Heilongjiang (CN); Liaowei Wu, Heilongjiang (CN); Chenlu Fan, Heilongjiang (CN); Qun Lou, Heilongjiang (CN); Mengyao Su, Heilongjiang (CN); Xin Zhang, Heilongjiang (CN); Zaihong Zhang, Heilongjiang (CN)

(73) Assignee: Harbin Medical University, Harbin (CN)

( * ) Notice: Subject to any disclaimer, the term of this patent is extended or adjusted under 35 U.S.C. 154(b) by 107 days.

(21) Appl. No.: 17/002,910

(22) Filed: Aug. 26, 2020

(65) Prior Publication Data
US 2021/0181097 A1 Jun. 17, 2021

(30) Foreign Application Priority Data
Dec. 16, 2019 (CN) .......................... 201911295676.7

(51) Int. Cl.
*G01N 21/33* (2006.01)
*G01N 33/18* (2006.01)

(52) U.S. Cl.
CPC .............. *G01N 21/33* (2013.01); *G01N 33/18* (2013.01); *G01N 33/182* (2013.01)

(58) Field of Classification Search
CPC ...... G01N 21/253; G01N 21/33; G01N 21/78; G01N 31/22; G01N 33/18; G01N 33/182
See application file for complete search history.

(56) References Cited

U.S. PATENT DOCUMENTS
6,589,796 B1  7/2003  Ohashi et al.

FOREIGN PATENT DOCUMENTS
| CN | 102507542 A | 6/2012 |
| CN | 204644342 A | 9/2015 |

OTHER PUBLICATIONS

Simple Microplate Method for Determination of Urinary Iodine, 2000, Clinical Chemistry, vol. 46: Issue 4, pp. 529-536 (Year: 2000).*

* cited by examiner

*Primary Examiner* — Jennifer Wecker
*Assistant Examiner* — Kathryn Elizabeth Limbaugh

(57) ABSTRACT

A method for detecting concentration of iodine in water samples. An arsenite-containing test solution, a tetravalent cerium ion-containing test solution and a series of iodine-containing standard solutions are prepared. The standard solutions are added to primary wells of a microplate, respectively. A water sample is added to a secondary well. The arsenite-containing test solution and the tetravalent cerium ion-containing test solution are sequentially added to the primary wells and the secondary well. Reaction mixture in each well is reacted and then measured for absorbance by a detector. A standard curve is plotted according to the absorbance of each primary well and a concentration of each iodine-containing standard solution. The absorbance of the sample is plugged into the standard curve to obtain an iodine concentration in the sample.

10 Claims, 1 Drawing Sheet

METHOD FOR DETECTING IODINE CONCENTRATION IN WATER SAMPLES

CROSS-REFERENCE TO RELATED APPLICATIONS

This application claims the benefit of priority from Chinese Patent Application No. 201911295676.7, filed on Dec. 16, 2019. The content of aforementioned application, including any intervening amendments thereto, is incorporated herein by reference in its entirety.

TECHNICAL FIELD

The invention relates to chemical detection, in particular to a method for detecting concentration of iodine in water samples.

BACKGROUND

Iodine content in drinking water, as an index for evaluating iodine nutrition status among the target population, is primarily used in the prevention and monitoring of iodine deficiency disorders. A national survey of iodine content in drinking water is carried out in 2017-2018, which involves nearly 400,000 water samples from more than 120,000 villages, more than 40,000 towns. Thus, there is still an urgent need to develop a novel method to accelerate the water iodine detection, facilitating the prevention and control of iodine deficiency disorders.

In recent years, the detection of iodine content in the water samples is performed mainly based on the method mentioned in GB/T5750.5-2006 (11.1) "Standard Examination Methods for Drinking Water-Nonmetal Parameters". This method has good detection specificity, high precision and accuracy, and low requirement for equipment, and is suitable for ordinary laboratories. However, the arsenic trioxide (commonly known as arsenic) used in this method (As(III)-$Ce^{4+}$ catalytic spectrophotometry) is highly toxic, and is under extremely strict control, so it is not readily available. Further, this method also produces a large amount of arsenic-containing waste liquid, which will seriously pollute the environment.

Inductively coupled plasma mass spectrometry (ICP-MS) has a rapid analysis and has been used in some laboratories. However, this method has high cost due to the use of expensive instruments, which limits its application in prefecture, city and country-level regions.

SUMMARY

An object of this application is to provide a method for detecting concentration of iodine in a water sample, which enables simple, rapid and economical detection, and can reduce waste production.

Technical solutions of this application are described as follows.

The invention provides a method for detecting iodine concentration in a water sample, comprising:
preparing a test solution A, a test solution B and an iodine-containing stock solution; and diluting the iodine-containing stock solution to prepare a series of iodine-containing standard solutions with different concentrations;
adding the iodine-containing standard solutions to a plurality of primary wells of a microplate, respectively; and adding the water sample to a secondary well of the microplate;
adding the test solution A to the primary wells respectively containing the iodine-containing standard solutions and the secondary well containing the water sample;
adding the test solution B to the primary wells respectively containing the iodine-containing standard solutions and the secondary well containing the water sample;
reacting the reaction mixture in each well;
after the reaction is completed, detecting an absorbance of the reaction mixture in each well under a preset wavelength by a detector;
plotting a standard curve according to the absorbance of each primary well and a concentration of each iodine-containing standard solution; and
plugging the absorbance of the reaction mixture in the secondary well into the standard curve to obtain an iodine concentration in the water sample;
wherein the test solution A is an arsenite-containing solution; the test solution B is a tetravalent cerium ion-containing solution; and the microplate comprises a plurality of wells with same shape, size and material. In an embodiment, wherein the detector is a microplate reader; and the microplate is a 96-well plate.

In an embodiment, the test solution A is an arsenous acid ($H_3AsO_3$) solution.

In an embodiment, a concentration of the $H_3AsO_3$ solution is 0.06 mol/L.

In an embodiment, the test solution B is an ammonium cerium sulfate solution.

In an embodiment, a concentration of tetravalent cerium ions in the ammonium sulfate ceric solution is 0.025 mol/L.

In an embodiment, the iodine-containing stock solution is a potassium iodide solution.

In an embodiment, a concentration of the potassium iodide solution is 100 μg/mL.

In an embodiment, after the test solution A is added, the microplate is cooled to 0-5° C.

In an embodiment, the iodine-containing standard solutions in the primary wells and the water sample in the secondary well have the same volume; equal volume of the test solution A is added to each primary well and the secondary well; equal volume of the test solution B is added to each primary well and the secondary well; and the reaction is performed at 25-40° C. under shaking; and the absorbance of each well is recorded when the primary well containing the largest iodine concentration reaches a preset absorbance.

In an embodiment, the preset wavelength is 400 nm.

Compared to the prior art, the invention has the following beneficial effects.

In the method provided herein for the detection of iodine concentration in water samples, the arsenic-cerium redox reaction catalyzed by iodine is performed in a microplate, which involves less consumption of reactants and catalyst, reducing the waste discharge, toxicity and cost. Due to the use of the microplate (such as a 96-well plate), the iodine standard curve can be obtained in one experiment, and at the same time, multiple samples also can be simultaneously detected, which greatly shortens the detection time, further lowering the cost. Compared to the ICP-MS, the microplate and the microplate reader have lower cost and are readily available. Moreover, this method has simple operation and high degree of automation, allowing for shortened detection time. The method is also suitable for the detection of a micro sample, which facilitates the standardization of the detection, rendering the detection results more reliable.

BRIEF DESCRIPTION OF THE DRAWINGS

The invention will be described below in detail with reference to the embodiments and accompanying drawings.

Obviously, the drawings merely illustrate some embodiments of the present application, and other embodiments obtained by those of ordinary skill in the art without sparing any creative effort should fall within the scope of the invention.

DETAILED DESCRIPTION OF EMBODIMENTS

The technical solutions in the embodiments of the application will be clearly and completely described below with reference to the drawings. Obviously, described below are only some embodiments of the application, rather than all the embodiments. Based on the embodiments disclosed herein, other embodiments obtained by those of ordinary skill in the art without sparing any creative work should fall within the scope of the application.

Figure 1:
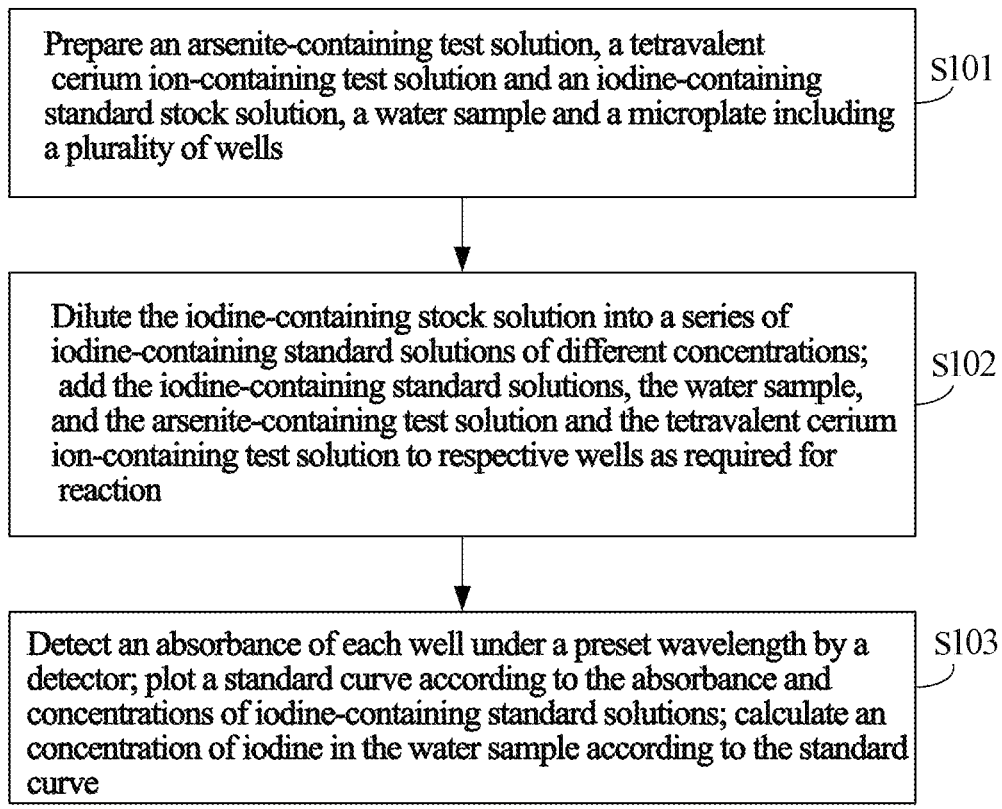
FIG. 1 is a flow chart of a method for detecting iodine concentration in a water sample according to an embodiment of the present invention.

FIG. 1 schematically shows a method for detecting iodine concentration in a water sample according to an embodiment of the invention, where the method includes:

S101: preparing a test solution A, a test solution B and a test solution C, a water sample and a microplate; where the test solution A is an arsenite-containing solution; the test solution B is a tetravalent cerium ion-containing solution; the test solution C is an iodine-containing standard stock solution; the microplate comprises a plurality of wells with same shape, size and material; and the material enables the light of a predetermined wavelength to pass through the microplate;

the test solution A is an arsenite-containing solution, such as arsenous acid solution ($H_3AsO_3$) and sodium arsenite solution ($Na_3AsO_3$); the test solution B is a tetravalent cerium ion-containing solution, such as ammonium cerium sulfate (($NH_4$)$_2$Ce($SO_4$)$_3$) solution and ammonium cerium nitrate (($NH_4$)$_2$Ce($NO_3$)$_6$); the test solution C is an iodine-containing standard stock solution, such as potassium iodide (KI) standard stock solution and potassium iodate ($KIO_3$) standard stock solution; and there is no special requirements for the concentration and preparation of the above test solutions;

the wells of the microplate serve not only as reaction vessels but also as cuvettes (the absorbance of the reaction mixture in the microwells needs to be measured at a predetermined wavelength); the material of the microplate cannot affect the measurement of absorbance within the predetermined wavelength range; the microplate is a 16-well, 48-well or 96-well plate, preferably the 96-well plate; the material is optically transparent pure polystyrene (PS); and the predetermined wavelength range refers to the detection wavelength range, preferably in the ultraviolet-visible light range of 300-700 nm;

S102: diluting the iodine-containing stock solution to prepare a series of iodine-containing standard solutions with different concentrations; adding the iodine-containing standard solutions to a plurality of primary wells of a microplate, respectively; and adding the water sample to a secondary well of the microplate; adding the test solution A to the primary wells respectively containing the iodine-containing standard solutions and the secondary well containing the water sample; adding the test solution B to the primary wells respectively containing the iodine-containing standard solutions and the secondary well containing the water sample; and reacting the reaction mixture in each well; as shown in the following scheme:

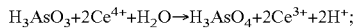

where this redox reaction is catalyzed by the iodine in the standard solution or in the sample to be detected;

the yellow $Ce^{4+}$ is reduced by arsenous acid to colorless $Ce^{3+}$; the higher the iodine content is, the faster the reaction rate and the less the remaining $Ce^{4+}$ are; the reaction temperature and time are controlled, and the absorbance of $Ce^{4+}$ remaining in the reaction system is measured at the predetermined wavelength to obtain the iodine content in the water sample;

the following requirements can be determined according to practical application: the concentration and the amount of each reactant; the concentration and amount of iodine-containing standard solution or the sample to be detected added into each well, the number of iodine-containing standard solutions with known concentration; the preparation of iodine standard solutions with different concentrations from the test solution C; the concentration and preparation of the iodine standard intermediate solution; whether the samples need to be diluted or not; total reaction volume; adding order; requirements for mixing and cooling; reaction conditions (temperature, time, etc.); and the degree of the reaction (that is, when the reaction mixture should be measured for the absorbance);

five or more iodine standard solutions with different concentrations are preferably provided for the plotting of the standard curve; the test solution C is diluted to prepare an iodine standard intermediate solution, which is then used as the iodine standard solution with the highest concentration in the series of standard solutions in a primary well; the next lower concentration standard solution is prepared by diluting the standard solution with the highest concentration, and the rest standard solutions are sequentially prepared in the same way; the iodine standard solutions in the primary wells share the same volume; when the concentration of iodine in the water sample exceeds the maximum concentration of the iodine standard solutions, the sample needs to be diluted, otherwise, the sample is directly measured; in one embodiment, in order to reduce error, arsenite ion and the iodine-containing standard solution or sample are added first, and then tetravalent cerium ion is added; the reaction mixture needs to be mixed uniformly; the temperature should be cooled to 0-5° C. before adding the tetravalent cerium; in an embodiment, the reaction is performed at about 30° C. for 15 min or until the absorbance of the primary well containing the maximum concentration of iodine lowers to about 0.15;

S103: after the reaction is completed, detecting an absorbance of each well under a preset wavelength by a detector; plotting a standard curve according to the absorbance of each primary well and a concentration of each iodine-containing standard solution; and plugging the absorbance of the reaction mixture in the secondary well into the standard curve to obtain an iodine concentration in the water sample;

the preset wavelength is within the predetermined wavelength range, and preferably a wavelength corresponding to the maximum absorption of $Ce^{4+}$; the preset wavelength is 400 nm, 405 nm or 420 nm; the preset wavelength can be determined according to the scanning results of the reaction system; the microplate is compatible with the detector to ensure that each of the wells containing the reaction mixture can be measured for the absorbance.

In an embodiment, the preset wavelength is 400 nm.

In an embodiment, the relationship between the iodine mass concentration and the absorbance value A is linearly fitted through regression equation:

$$c = a + b\lg A \text{ (or } c = a + b\ln A)$$

where c (μg/L) is the mass concentration of iodine in the iodine-containing standard solution (or the water sample); a is the intercept of the standard curve; b is the lope of the standard curve; A is the measured absorbance value of the iodine-containing standard solution (or the sample to be detected).

The regression equation of the standard curve is obtained according to the above linear relationship. Then the absorbance value of the sample is plugged into the regression equation to obtain the mass concentration of iodine in the sample.

In the method provided herein for the detection of iodine concentration in water samples, the arsenic-cerium redox reaction catalyzed by iodine is performed in a microplate, which involves less consumption of reactants and catalyst, reducing the waste discharge, toxicity and cost. Due to the use of the microplate (such as a 96-well plate), the standard curve of iodine concentration can be obtained in one time, and at the same time, multiple samples also can be detected, which greatly shortens the detection time, further lowering the cost. Compared to the ICP-MS, the microplate and the microplate reader have lower cost and are readily available. Moreover, this method has simple operation and high degree of automation, allowing for shortened detection time. The method is also suitable for the detection of a micro sample, which facilitates the standardization of the detection, rendering the detection results more reliable.

In an embodiment, the detector is a microplate reader and the microplate is a 96-well plate.

A microplate reader is employed in the above iodine detection, which has advantages of less consumption of sample and reagents, rapid detection and less waste discharge. Therefore, the invention not only reduces the cost, but also largely lowers the consumption of samples and toxic reagents and the waste discharge, which has important significance and practical application value for the monitoring of samples in large size in the disease prevention and control. The method of the invention is suitable for the application in city and county-level laboratories, promoting the full coverage of the iodine detection. 96-well plates are widely used for the simultaneous detection of a large number of samples.

In an embodiment, the test solution A is an arsenous acid ($H_3AsO_3$) solution. In an embodiment, a concentration of the arsenous acid solution is 0.06 mol/L.

The preparation of the 0.06 mol/L $H_3AsO_3$ solution is described as follows. 0.6 g of arsenic trioxide, 4 g of sodium chloride and 0.2 g of sodium hydroxide are added into a beaker, to which about 50 mL of pure water is added. The mixture is heated for complete dissolution and then cooled to room temperature. Further, 20 mL of sulfuric acid solution (2.5 mol/L) is slowly added, and the reaction mixture is cooled to room temperature, diluted to 100 mL with pure water and stored in a brown bottle for use. The $H_3AsO_3$ solution can be stored for 6 months at room temperature.

In an embodiment, the test solution B is an ammonium cerium sulfate solution. In an embodiment, a concentration of tetravalent cerium ions in the ammonium cerium sulfate solution is 0.025 mol/L.

The preparation of the 0.025 mol/L ammonium cerium sulfate solution is described as follows. 1.58 g of ammonium cerium sulfate or 1.67 g of ammonium cerium sulfate tetrahydrate is dissolved in 70 mL of 2.5 mol/L sulfuric acid solution, and the resulting solution is diluted with pure water to 100 mL and stored in a brown bottle. The ammonium cerium sulfate solution can be stored for 6 months at room temperature.

In an embodiment, the test solution C is a potassium iodide solution. In an embodiment, a concentration of iodide ions in the potassium iodide solution is 100 μg/mL.

The preparation of the 100 μg/mL potassium iodide solution is described as follows. 0.1686 g of potassium iodide that has been dried at 105-110° C. is dissolved in pure water and diluted with pure water to 1000 mL to produce the 100 μg/mL potassium iodide solution. The potassium iodide solution can be stored in a tightly stoppered brown bottle at 4° C. for 6 months.

Figure 2:
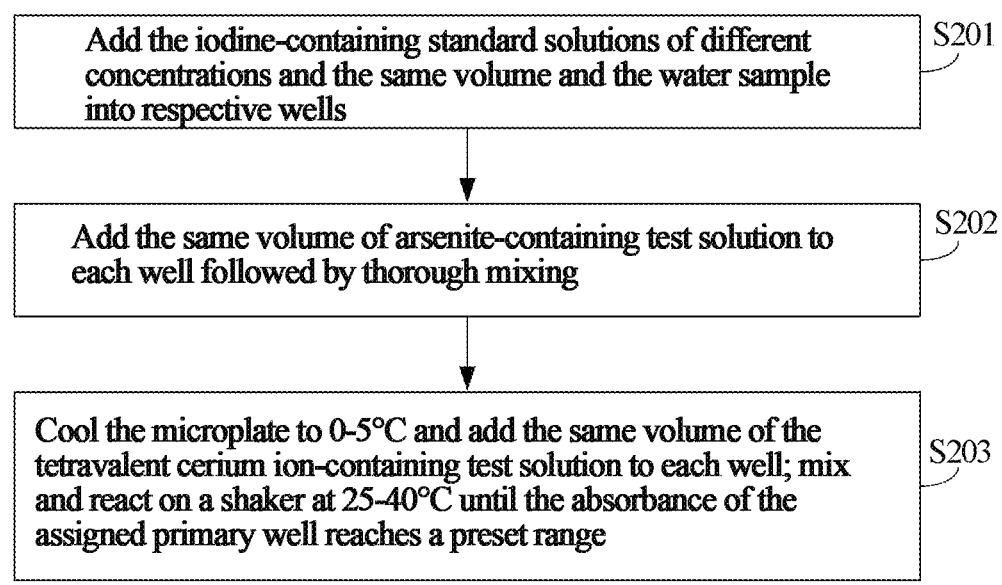
FIG. 2 is a flow chart of the method for detecting iodine concentration in a water sample according to an embodiment of the present invention.

In an embodiment as illustrated in FIG. 2, the step (S102) specifically includes:

S201: adding the iodine-containing standard solutions with different concentrations to a plurality of primary wells, respectively; and adding the water sample into a secondary well; where the iodine-containing standard solutions and the sample have the same volume;

S202: adding the test solution A to each well in equal volume followed by mixing thoroughly; and S203: cooling the microplate to 0-5° C. (such as 0° C., 3° C. and 5° C.) and adding the test solution B to each well in equal volume; mixing and reacting the reaction mixture on a shaker at 25-40° C. (such as 25° C., 32° C. and 40° C.) until the absorbance of the assigned primary well reaches a preset range.

The details of the method provided herein are specifically described below.

(1) Preparation of Test Solutions

The test solution A, test solution B, test solution C and iodine standard intermediate solution with a concentration of 300 μg/L are prepared as follows.

The test solution A is a 0.06 mol/L arsenous acid solution, which is prepared as follows. 0.6 g of arsenic trioxide, 4 g of sodium chloride and 0.2 g of sodium hydroxide are added in a beaker, to which about 50 mL of pure water is added. The mixture is heated for complete dissolution and then cooled to room temperature. Further, 20 mL of a 2.5 mol/L sulfuric acid solution is slowly added, and the reaction mixture is cooled to room temperature, diluted to 100 mL with pure water and stored in a brown bottle for use. The $H_3AsO_3$ solution can be stored at room temperature for 6 months.

The test solution B is an ammonium cerium sulfate solution ($c(Ce^{4+})=0.025$ mol/L), which is prepared as follows. 1.58 g of ammonium cerium sulfate or 1.67 g of ammonium cerium sulfate tetrahydrate is dissolved in 70 mL of 2.5 mol/L sulfuric acid solution, and the resulting solution is diluted with pure water to 100 mL and stored in a brown bottle.

The test solution C is an iodide-containing standard stock solution (p(I)=100 μg/mL), which is prepared as follows. 0.1686 g of potassium iodide that has been dried at 105-110° C. is dissolved and diluted with pure water to 1000 mL to produce the 100 μg/mL potassium iodide solution. The potassium iodide solution can be stored in a tightly stoppered brown bottle at 4° C. for 6 months.

(2) Addition of Sample

A. 8 wells of the 96-well plate are selected as primary wells and different volumes of the iodine standard intermediate solution are added to the primary wells, respectively, and then diluted to a final volume of 25 μL. The volumes of the iodine standard intermediate solutions are such that the iodine ion concentrations in the primary wells are 300 μg/L, 300*2/3 μg/L, 300*4/9 μg/L, 300*8/27 μg/L, 300*16/81 μg/L, 300*32/243 μg/L, 300*64/729 μg/L, and 0 μg/L, respectively.

B. Some wells in the remaining wells of the 96-well plate are selected as secondary wells, to which 25 μL, of the water sample is added.

C. 125.0 μL of the test solution A is added into each well, and the reaction mixture in each well is mixed thoroughly.

D. The 96-well plate is cooled to 4° C., and 50 μL of the test solution B is added into each well. Thereafter, the 96-well plate is shaken on a shaker and programmatically heated to 30° C. for reaction.

(3) Measurement

When the absorbance of the first primary well (i.e., the primary well containing the largest iodine concentration) reaches about 0.15, the absorbance of each well is measured at 400 nm.

(4) Calculation

A standard curve is plotted in a semi-logarithmic coordinate system, in which the abscissa is the concentration of the iodine standard solution in the primary well, and the ordinate is the logarithm of the measured absorbance A. The measured absorbance of each secondary well is plugged into the standard curve to obtain the mass concentration of iodine in the sample.

Compared with existing methods for detecting iodine, the method of the invention has the following advantages.

1. Compared with the traditional spectrophotometry, the method of the invention uses a microplate reader to detect the content of iodine in a sample, which greatly reduces the consumption of samples and test reagents, and also diminishes the use of arsenic trioxide and the production of toxic waste, avoiding the environmental pollution.

2. The combination of microplate reader and 96-well plate enables the simultaneous detection of multiple samples, which greatly shortens detection time and facilitates the detection of samples in larger size, facilitating realizing the miniaturization of accurate, fast, small sample and high throughput detection and providing support for the manufacture of related kits.

3. The combination of microplate reader and 96-well plate significantly lowers the cost and improve the detection efficiency. Through the selection of wavelength and linear range of the standard curve and the optimization of concentration and ratio of reagents, reaction time and temperature, the method of the invention enables the miniaturization of the sample to be detected and the rapid and high-throughput detection.

The advantages and features of the invention will be further described and verified below with reference to the embodiments.

Example 1

A sample with an iodine concentration of 50.9±2.3 μg/L was used herein as a sample to be detected. Further, 8 primary wells were selected for plotting the standard curve and 24 secondary wells were selected for the detection of the sample.

(1) Preparation of Test Solutions

The test solution A, test solution B, test solution C and iodine standard intermediate solution with a concentration of 300 μg/L were prepared as follows.

The test solution A was a 0.06 mol/L arsenous acid solution which was prepared as follows. 0.6 g of arsenic trioxide, 4 g of sodium chloride and 0.2 g of sodium hydroxide were dissolved in about 50 mL of pure water under heating. The reaction mixture was cooled to room temperature, slowly added with 20 mL of sulfuric acid solution (2.5 mol/L), cooled to room temperature, diluted to 100 mL with pure water and stored in a brown bottle. The prepared arsenous acid solution can be stored at room temperature for 6 months.

The test solution B was an ammonium cerium sulfate solution ($c(Ce^{4+})$=0.025 mol/L), which was prepared as follows. 1.58 g of ammonium cerium sulfate or 1.67 g of ammonium cerium sulfate tetrahydrate was dissolved in 70 mL of sulfuric acid solution ($c(H_2SO_4)$=2.5 mol/L), diluted with pure water to 100 mL and stored in a brown bottle. The prepared ammonium cerium sulfate solution can be stored at room temperature for 6 months.

The test solution C was an iodide standard stock solution ($p(I)$=100 μg/mL), which was prepared as follows. 0.1686 g of potassium iodide that had been dried at 105-110° C. was dissolved in pure water, diluted with pure water to 1000 mL and stored in a tightly stoppered brown bottle, which can be stored at 4° C. for 6 months. Before use, 30 μL of the test solution C was pipetted, placed in a 10 mL volumetric flask and diluted with pure water to the graduation to prepare the 300 μg/L iodine standard intermediate solution.

0.4 mL of an environmental standard sample (batch number: B1903019) was accurately pipetted and diluted to 10 mL in a volumetric flask to obtain a solution with an iodide ion concentration of 5.09±0.23 mg/L. Thereafter, 100.0 μL of the solution was pipetted and diluted with pure water to the graduation in a 10 mL volumetric flask to obtain the sample with a concentration of 50.9±2.3 μg/L.

(2) Addition of Samples

A. 8 wells of the 96-well plate were selected as primary wells. 75 μL, of the iodine standard intermediate solution with a concentration of 300 μg/L was added into the first primary well, and the rest primary wells were added with 25 μL, of deionized water, respectively. Then 50 μL of the solution was accurately pipetted from the first primary well to the second primary well by a micropipette, and then the reaction mixture in the second primary well was fully mixed. Thereafter, 50 μL of the solution in the second primary well was accurately pipetted to the third primary well and fully mixed with the water and so on. Finally, 50 μL of the solution in the seventh primary well was discarded, so that the volume of the solution in each primary well was 25 μL, and the iodine ion concentrations in the primary wells were 300 μg/L, 300*2/3 μg/L, 300*4/9 μg/L, 300*8/27 μg/L, 300*16/81 μg/L, 300*32/243 μg/L, 300*64/729 μg/L, and 0 μg/L, respectively.

B. The 24 secondary wells were added with 25 μL of the sample, respectively.

C. 125.0 μL of the test solution A was added into each primary well and secondary well, and the reaction mixture in each well was mixed thoroughly.

D. The 96-well plate was cooled to 4° C. and 50 μL of the test solution B was added into each well. Then the plate was shaken on the shaker and programmatically heated to 30° C. to react the reaction mixture in each well for about 25 min.

(3) Measurement

When the absorbance of the first primary well (that is, the primary well with the largest iodide ion level) reached about 0.15, the absorbance of each well was measured at a wavelength of 400 nm. The results were shown in Table 1.

TABLE 1

Absorbance of sample in Example 1

| Well number | First column (Primary well) | Second column (Secondary well) | Third column (Secondary well) | Fourth column (Secondary well) |
|---|---|---|---|---|
| A | 0.142 | 1.539 | 1.519 | 1.528 |
| B | 0.37 | 1.525 | 1.508 | 1.495 |
| C | 0.65 | 1.491 | 1.543 | 1.483 |
| D | 1.05 | 1.517 | 1.541 | 1.482 |
| E | 1.391 | 1.544 | 1.512 | 1.522 |
| F | 1.774 | 1.527 | 1.528 | 1.478 |
| G | 1.925 | 1.483 | 1.551 | 1.544 |
| H | 2.476 | 1.494 | 1.499 | 1.476 |

(4) Calculation

The iodine concentrations in the wells A-H of the first column (300 µg/L, 300*2/3 µg/L, 300*4/9 µg/L, 300*8/27 µg/L, 300*16/81 µg/L, 300*32/243 µg/L, 300*64/729 µg/L, and 0 µg/L) were adopted as the abscissa and the logarithm of the measured absorbance values of the wells A-H of the first column was adopted as the ordinate to plot a standard curve in a semi-logarithmic coordinate system, where the obtained standard curve had a regression equation of $y=-0.0042x+0.3936$ with a correlation coefficient $R^2$ of 0.9991.

The absorbance of each of the 24 secondary wells was plugged into the standard curve to calculate the iodine ion concentration in the sample. The results were shown in table 2.

TABLE 2

Concentration of iodine ions in sample (µg/L)

| Well number | First column (Primary well) | Second column (Secondary well) | Third column (Secondary well) | Fourth column (Secondary well) |
|---|---|---|---|---|
| A | 300 | 49.1 | 50.5 | 49.9 |
| B | 300*2/3 | 50.1 | 51.2 | 52.1 |
| C | 300*4/9 | 52.4 | 48.9 | 53.0 |
| D | 300*8/27 | 50.6 | 49.0 | 53.0 |
| E | 300*16/81 | 48.8 | 51.0 | 50.3 |
| F | 300*32/243 | 49.9 | 49.9 | 53.3 |
| G | 300*64/729 | 53.0 | 48.3 | 48.8 |
| H | 0 | 52.2 | 51.9 | 53.5 |

It can be obtained from the above results that the average iodine ion concentration of the sample was 50.9±1.6 g/L with coefficient of variation (CV) of 3.1%.

Example 2

A sample having a concentration of 50.9±2.3 µg/L was measured herein. Further, 8 primary wells were selected for plotting the standard curve and 24 secondary wells were selected for the detection of the sample.

(1) Preparation of Test Solutions

The test solution A, test solution B, test solution C and iodine standard intermediate solution with a concentration of 300 µg/L were prepared as follows.

Before use, 30 µL of the test solution C was pipetted to a 10 mL volumetric flask and diluted with pure water to the graduation to prepare the 300 µg/L iodine standard intermediate solution.

100.0 µL of the diluted environmental standard sample solution with an iodide ion concentration of 5.09±0.23 mg/L was pipetted and diluted with pure water to the graduation in a 10 mL volumetric flask to obtain the sample with a concentration of 50.9±2.3 µg/L.

(2) Sample Addition

A. 8 wells of the 96-well plate were selected as primary wells. 75 µL of the iodine standard intermediate solution with a concentration of 300 µg/L was added into the first primary well, and the rest primary wells were added with 25 µL of deionized water, respectively. Then 50 µL of the solution was accurately pipetted from the first primary well to the second primary well by a micropipette, and then the reaction mixture in the second primary well was fully mixed. Thereafter, 50 µL of the solution in the second primary well was accurately pipetted to the third primary well and fully mixed with the water and so on. Finally, 50 µL of the solution in the seventh primary well was discarded, so that the volume of the solution in each primary well was 25 µL, and the iodine ion concentrations in the primary well were 300 µg/L, 300*2/3 µg/L, 300*4/9 µg/L, 300*8/27 µg/L, 300*16/81 µg/L, 300*32/243 µg/L, 300*64/729 µg/L, and 0 µg/L, respectively.

B. The 24 secondary wells were added with 25 µL of the sample, respectively.

C. 125.0 µL of the test solution A was added into each primary well and secondary well, and the reaction mixture in each well was mixed thoroughly.

D. The 96-well plate was cooled to 4° C. and 50 µL of the test solution B was added into each well. Then the plate was shaken on the shaker and programmatically heated to 30° C. to react the reaction mixture in each well for about 25 min.

(3) Measurement

When the absorbance of the first primary well (that is, the primary well with the largest iodide ion level) reached about 0.15, the absorbance of each well was measured at a wavelength of 400 nm. The results were shown in Table 3.

TABLE 3

Absorbance of sample in Example 2

| Well number | First column (Primary well) | Second column (Secondary well) | Third column (Secondary well) | Fourth column (Secondary well) |
|---|---|---|---|---|
| A | 0.13 | 1.506 | 1.485 | 1.506 |
| B | 0.339 | 1.467 | 1.515 | 1.462 |
| C | 0.67 | 1.49 | 1.468 | 1.496 |
| D | 0.987 | 1.469 | 1.526 | 1.498 |
| E | 1.35 | 1.509 | 1.499 | 1.511 |
| F | 1.717 | 1.466 | 1.495 | 1.534 |
| G | 1.951 | 1.519 | 1.509 | 1.478 |
| H | 2.446 | 1.492 | 1.495 | 1.487 |

(4) Calculation

The iodine concentrations in the wells A-H of the first column (300 µg/L, 300*2/3 µg/L, 300*4/9 µg/L, 300*8/27 µg/L, 300*16/81 µg/L, 300*32/243 µg/L, 300*64/729 µg/L, and 0 µg/L) were adopted as the abscissa and the logarithm of the measured absorbance values of the wells A-H of the first column was adopted as the ordinate to plot a standard curve in a semi-logarithmic coordinate system, where the obtained standard curve had a regression equation of $y=-0.0042x+0.3917$, and a correlation coefficient $R^2$ of 0.9994.

The absorbance of each of the 24 secondary wells was plugged into the standard curve to calculate the iodine ion concentration in the sample. The results were shown in table 4.

TABLE 4

Concentration of iodine ions in sample (μg/L)

| Well number | First column (Primary well) | Second column (Secondary well) | Third column (Secondary well) | Fourth column (Secondary well) |
|---|---|---|---|---|
| A | 300 | 49.7 | 51.2 | 49.7 |
| B | 300*2/3 | 52.4 | 49.1 | 52.7 |
| C | 300*4/9 | 50.8 | 52.3 | 50.4 |
| D | 300*8/27 | 52.3 | 48.4 | 50.3 |
| E | 300*16/81 | 49.5 | 50.2 | 49.4 |
| F | 300*32/243 | 52.5 | 50.5 | 47.9 |
| G | 300*64/729 | 48.9 | 49.5 | 51.6 |
| H | 0 | 50.7 | 50.5 | 51.0 |

It can be obtained from the above results that the average iodine ion concentration of the sample to be detected was 50.5±1.3 μg/L with coefficient of variation (CV) of 2.6%.

Example 3

A sample with a concentration of 124±12.4 μg/L was measured herein. Further, 8 primary wells were selected for plotting the standard curve and 24 secondary wells were selected for the detection of the sample.

(1) Preparation of Test Solutions

The test solution A, test solution B, test solution C and iodine standard intermediate solution with a concentration of 300 μg/L were prepared as follows.

Before use, 30 μL of the test solution C was pipetted, placed in a 10 ml volumetric flask and diluted with pure water to the graduation to prepare the 300 μg/L iodine standard intermediate solution.

0.2 mL of an environmental standard sample solution was pipetted and diluted in a 10 mL volumetric flask to obtain a solution with an iodide ion concentration of 124±12.4 μg/L.

(2) Addition of Samples

A. 8 wells of the 96-well plate were selected as primary wells. 75 μg/L of the iodine standard intermediate solution with a concentration of 300 μg/L was added into the first primary well, and the rest primary wells were added with 25 μL of deionized water, respectively. Then 50 μL of the solution was accurately pipetted from the first primary well to the second primary well by a micropipette, and then the reaction mixture in the second primary well was fully mixed. Thereafter, 50 μL of the solution in the second primary well was accurately pipetted to the third primary well and fully mixed with the water and so on. Finally, 50 μL of the solution in the seventh primary well was discarded, so that the volume of the solution in each primary well was 25 μL and the iodine ion concentrations in the primary well were 300 μg/L, 300*2/3 μg/L, 300*4/9 μg/L, 300*8/27 μg/L, 300*16/81 μg/L, 300*32/243 μg/L, 300*64/729 μg/L, and 0 μg/L, respectively.

B. The 24 secondary wells were added with 25 μL of the sample, respectively.

C. 125.0 μL of the test solution A was added into each primary well and secondary well, and the reaction mixture in each well was mixed thoroughly.

D. The 96-well plate was cooled to 4° C. and 50 μL of the test solution B was added into each well. Then the plate was shaken on the shaker and programmatically heated to 30° C. to react the reaction mixture in each well for about 25 min.

(3) Measurement

When the absorbance of the first primary well (that is, the primary well with the largest iodide ion level) reached about 0.15, the absorbance of each well was measured at a wavelength of 400 nm. The results were shown in Table 5.

TABLE 5

Absorbance of sample in Example 3

| Well number | First column (Primary well) | Second column (Secondary well) | Third column (Secondary well) | Fourth column (Secondary well) |
|---|---|---|---|---|
| A | 0.15 | 0.773 | 0.753 | 0.726 |
| B | 0.369 | 0.816 | 0.742 | 0.744 |
| C | 0.671 | 0.827 | 0.851 | 0.717 |
| D | 0.978 | 0.833 | 0.828 | 0.767 |
| E | 1.352 | 0.754 | 0.754 | 0.817 |
| F | 1.617 | 0.737 | 0.762 | 0.697 |
| G | 1.851 | 0.846 | 0.772 | 0.774 |
| H | 2.346 | 0.797 | 0.816 | 0.725 |

(4) Calculation

The iodine concentrations in the wells A-H of the first column (300 μg/L, 300*2/3 μg/L, 300*4/9 μg/L, 300*8/27 μg/L, 300*16/81 μg/L, 300*32/243 μg/L, 300*64/729 μg/L, and 0 μg/L) were adopted as the abscissa and the logarithm of the measured absorbance values of the wells A-H of the first column was adopted as the ordinate to plot a standard curve in a semi-logarithmic coordinate system, where the obtained standard curve had a regression equation of $y=-0.004x+0.3642$ and a correlation coefficient $R^2$ of 0.9995.

The absorbance of each of the 24 secondary wells was plugged into the standard curve to calculate the iodine ion concentration in the sample. The results were shown in table 6.

TABLE 6

Concentration of iodine ions in sample (μg/L)

| Well number | First column (Primary well) | Second column (Secondary well) | Third column (Secondary well) | Fourth column (Secondary well) |
|---|---|---|---|---|
| A | 300 | 119.0 | 121.9 | 125.8 |
| B | 300*2/3 | 113.1 | 123.4 | 123.2 |
| C | 300*4/9 | 111.7 | 108.6 | 127.2 |
| D | 300*8/27 | 110.9 | 111.5 | 119.9 |
| E | 300*16/81 | 121.7 | 121.7 | 113.0 |
| F | 300*32/243 | 124.2 | 120.6 | 130.2 |
| G | 300*64/729 | 109.2 | 119.1 | 118.9 |
| H | 0 | 115.7 | 113.1 | 126.0 |

It can be obtained from the above results that the average iodine ion concentration of the sample to be detected was 118.7±6.2 μg/L with coefficient of variation (CV) of 5.2%.

Example 4

A sample with a concentration of 50.9±2.3 μg/L was measured herein. Further, 8 primary wells were selected for plotting the standard curve and 24 secondary wells were selected for the detection of the sample and the sample spiked with 50 μg/L of the standard solution.

(1) Preparation of Test Solutions

The test solution A, test solution B, test solution C and iodine standard intermediate solution with a concentration of 300 μg/L were prepared as follows.

Before use, 30 μL of the test solution C was pipetted to a 10 mL volumetric flask and diluted with pure water to the graduation to prepare the 300 μg/L iodine standard intermediate solution.

100.0 μL of the diluted environmental standard sample solution with an iodide ion concentration of 5.09±0.23 mg/L was pipetted and diluted with pure water to the graduation in a 10 mL volumetric flask to obtain the sample with a concentration of 50.9±2.3 μg/L.

1 mL of the iodine standard intermediate solution with a concentration of 300 μg/L was pipetted and mixed with 5 mL of water to obtain a 50 μg/L iodine standard solution.

(2) Addition of Sample

A. 8 wells of the 96-well plate were selected as primary wells. 75 μL, of the iodine standard intermediate solution with a concentration of 300 μL was added into the first primary well, and the rest primary wells were added with 25 μL of deionized water, respectively. Then 50 μL of the solution was accurately pipetted from the first primary well to the second primary well by a micropipette, and then the reaction mixture in the second primary well was fully mixed. Thereafter, 50 μg/L of the solution in the second primary well was accurately pipetted to the third primary well and fully mixed with the water and so on. Finally, 50 μL of the solution in the seventh primary well was discarded, so that the volume of the solution in each primary well was 25 μL and the iodine ion concentrations in the primary wells were 300 μg/L, 300*2/3 μg/L, 300*4/9 μg/L, 300*8/27 μg/L, 300*16/81 μg/L, 300*32/243 μg/L, 300*64/729 μg/L, and 0 μg/L, respectively.

B. The secondary wells of the second column were added with 25 μL of the sample to be detected, respectively. The secondary wells of the third column were added with 25 μL of the sample to be detected and 25 μL of the standard solution having a concentration of 50 μg/L. The mixture in each secondary well of the third column was pipetted into the secondary well of the fourth column.

C. 125.0 μL of the test solution A was added into each primary well and secondary well, and the reaction mixture in each well was mixed thoroughly.

D. The 96-well plate was cooled to 4° C. and 50 μL of the test solution B was added into each well. Then the plate was shaken on the shaker and programmatically heated to 30° C. to react the reaction mixture in each well for about 25 min.

(3) Measurement

When the absorbance of the first primary well (that is, the primary well with the largest iodide ion level) reached about 0.15, the absorbance of each well was measured at a wavelength of 400 nm. The results were shown in Table 7.

TABLE 7

Absorbance of sample in Example 4

| Well number | First column (Primary well) | Second column (Secondary well) | Third column (Secondary well) | Fourth column (Secondary well) |
|---|---|---|---|---|
| A | 0.159 | 1.497 | 1.523 | 1.486 |
| B | 0.379 | 1.518 | 1.512 | 1.491 |
| C | 0.701 | 1.519 | 1.495 | 1.504 |
| D | 1.062 | 1.502 | 1.476 | 1.534 |
| E | 1.392 | 1.527 | 1.519 | 1.476 |
| F | 1.654 | 1.489 | 1.468 | 1.529 |
| G | 1.925 | 1.484 | 1.497 | 1.509 |
| H | 2.395 | 1.525 | 1.489 | 1.517 |

(4) Calculation

The iodine concentrations in the wells A-H of the first column (300 μg/L, 300*2/3 μg/L, 300*4/9 μg/L, 300*8/27 μg/L, 300*16/81 μg/L, 300*32/243 μg/L, 300*64/729 μg/L, and 0 μg/L) were adopted as the abscissa and the logarithm of the measured absorbance values of the wells A-H of the first column was adopted as the ordinate to plot a standard curve in a semi-logarithmic coordinate system, where the obtained standard curve had a regression equation of $y=-0.0042x+0.3917$ with a correlation coefficient $R^2$ of 0.9994.

The absorbance of each of the 24 secondary wells was plugged into the standard curve to calculate the iodine ion concentration in the sample. The results were shown in Table 8.

TABLE 8

Concentration of iodine ions in sample (μg/L)

| Well number | First column (Primary well) | Second column (Secondary well) | Third column (Secondary well) | Fourth column (Secondary well) |
|---|---|---|---|---|
| A | 300 | 50.8 | 48.9 | 51.6 |
| B | 300*2/3 | 52.2 | 49.7 | 51.2 |
| C | 300*4/9 | 49.2 | 50.9 | 50.3 |
| D | 300*8/27 | 50.4 | 52.3 | 48.1 |
| E | 300*16/81 | 49.3 | 49.2 | 52.3 |
| F | 300*32/243 | 49.9 | 52.9 | 48.5 |
| G | 300*64/729 | 51.7 | 50.8 | 49.9 |
| H | 0 | 48.8 | 51.4 | 49.3 |

It can be obtained based on the above results that the average iodine ion concentration of the sample was 50.3 μg/L (standard deviation: 1.2 μg/L; coefficient of variation (CV)=2.4%), and the average iodine ion concentration of the sample after spiked was 50.4 μg/L (standard deviation: 1.4 μg/L; coefficient of variation (CV)=2.8%) The spike recovery rate was (50.4*2−50.3)/50=101.0%.

It can be demonstrated by the above embodiments that the method of the invention for detecting the content of iodine has desirable accuracy and reproducibility.

Described above are only preferred embodiments of the invention, and are not intended to limit the scope of the invention. Any modification, replacement and change made without departing from the spirit of the invention should fall within the scope of the invention.

What is claimed is:

1. A method for detecting concentration of iodine in a water sample, consisting of:
preparing a test solution A, a test solution B and an iodine-containing stock solution; and diluting the iodine-containing stock solution to prepare a series of iodine-containing standard solutions with different concentrations;
adding the iodine-containing standard solutions to a plurality of primary wells of a microplate, respectively; and adding the water sample to a secondary well of the microplate;
adding the test solution A to the primary webs respectively containing the iodine-containing standard solutions and the secondary well containing the water sample;
after the test solution A is added, cooling the microplate to 0-5° C., and then adding the test solution B to the primary wells respectively containing the iodine-containing standard solutions and the secondary well containing the water sample;
reacting the reaction mixture in each well at 25-40° C. under shaking;
after the reaction is completed, detecting an absorbance of the reaction mixture in each well under a preset wavelength by a microplate reader;

plotting a standard curve according to the absorbance of each primary well and a concentration of each iodine-containing standard solution; and plugging the absorbance of the water sample into the standard curve to obtain an iodine concentration in the water sampled;

wherein the test solution A is an arsenite-containing solution; the test solution B is a tetravalent cerium ion-containing solution; and the microplate comprises a plurality of wells with same shape, size and material.

2. The method of claim 1, wherein the microplate is a 96-well plate.

3. The method of claim 1, wherein the test solution A is an arsenous acid ($H_3AsO_3$) solution.

4. The method of claim 3, wherein a concentration of the $H_3AsO_3$ solution is 0.06 mol/L.

5. The method of claim 1, wherein the test solution B is an ammonium cerium sulfate solution.

6. The method of claim 5, wherein a concentration of tetravalent cerium ions in the ammonium cerium sulfate solution is 0.025 mol/L.

7. The method of claim 1, wherein the iodine-containing stock solution is a potassium iodide solution.

8. The method of claim 7, wherein a concentration of the potassium iodide solution is 100 μg/mL.

9. The method of claim 1, wherein the iodine-containing standard solutions in the primary wells and the water sample in the secondary well have the same volume; the test solution A is added to each primary well and the secondary well in equal volume; the test solution B is added to each primary well and the secondary well in equal volume; and the absorbance of each well is recorded when the primary well containing the largest iodine concentration reaches a preset absorbance.

10. The method of claim 1, wherein the preset wavelength is 400 nm.

* * * * *